(12) United States Patent
El-Baz et al.

(10) Patent No.: US 11,151,717 B2
(45) Date of Patent: Oct. 19, 2021

(54) COMPUTER AIDED DIAGNOSIS SYSTEM FOR MILD COGNITIVE IMPAIRMENT

(71) Applicant: UNIVERSITY OF LOUISVILLE RESEARCH FOUNDATION, INC., Louisville, KY (US)

(72) Inventors: Ayman S. El-Baz, Louisville, KY (US); Fatmaelzahraa El-Gamal, Mansoura (EG); Mohammed Elmogy, Mansoura (EG); Gregory N. Barnes, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 190 days.

(21) Appl. No.: 16/658,420

(22) Filed: Oct. 21, 2019

(65) Prior Publication Data

US 2020/0126221 A1    Apr. 23, 2020

Related U.S. Application Data

(60) Provisional application No. 62/747,716, filed on Oct. 19, 2018.

(51) Int. Cl.
*G06T 7/00* (2017.01)
*G16H 50/20* (2018.01)
(Continued)

(52) U.S. Cl.
CPC ........... *G06T 7/0012* (2013.01); *G06N 20/10* (2019.01); *G16H 30/20* (2018.01); *G16H 30/40* (2018.01);
(Continued)

(58) Field of Classification Search
CPC ......... G06T 7/0012; G06T 2207/10088; G06T 2207/10104; G06T 2207/20076;
(Continued)

(56) References Cited

U.S. PATENT DOCUMENTS

| | | | | |
|---|---|---|---|---|
| 2009/0292557 | A1* | 11/2009 | Sirohey | G06F 19/00 705/3 |
| 2018/0204327 | A1* | 7/2018 | Matthews | G06K 9/00147 |
| 2018/0310869 | A1* | 11/2018 | Yablonskiy | A61B 5/055 |

OTHER PUBLICATIONS

Samsad Beagum et al., "Alzheimer's disease, bio-markers, and the role of classification techniques in early diagnosis from neuroimages—An analysis", 2016 IEEE International Conference on Computational Intelligence and Computing Research (ICCIC), Dec. 15-17, 2016, pp. 1-6 (Year: 2016).*

(Continued)

*Primary Examiner* — Nay A Maung
*Assistant Examiner* — Jose M Torres
(74) *Attorney, Agent, or Firm* — Dentons Bingham Greenebaum LLP; Brian W. Chellgren

(57) ABSTRACT

A non-invasive computer-aided diagnosis system generates a diagnosis of mild cognitive impairment, a disease state which often leads to the development of Alzheimer's disease. The system uses as inputs both functional positron emission tomography and structural magnetic resonance imaging data, reconstructs a model of the patient's cortex, uses machine-learning techniques to generate probabilities for mild cognitive impairments for local cortical regions, uses machine-learning techniques to fuse the local diagnoses to generate a global diagnosis based on each imaging modality, then uses machine-learning techniques to fuse the modality-specific global diagnoses to generate a final global diagnosis.

20 Claims, 6 Drawing Sheets

(51) Int. Cl.
*G16H 30/20* (2018.01)
*G06N 20/10* (2019.01)
*G16H 30/40* (2018.01)

(52) U.S. Cl.
CPC ... *G16H 50/20* (2018.01); *G06T 2207/10088* (2013.01); *G06T 2207/10104* (2013.01); *G06T 2207/30016* (2013.01)

(58) Field of Classification Search
CPC . G06T 2207/20084; G06T 2207/30016; G06T 2207/04; G16H 30/20; G16H 30/40; G16H 50/20; G16H 50/50; G06N 20/10
See application file for complete search history.

(56) References Cited

OTHER PUBLICATIONS

Martinez-Torteya et al., "Improved Diagnostic Multimodal Biomarkers for Alzheimer's Disease and Mild Cognitive Impairment", BioMed Research International, vol. 2015, Article ID 961314, pp. 1-11 (Year: 2015).*

Jack Jr. et al., "11C PiB and structural MRI provide complementary information in imaging of Alzheimer's disease and amnestic mild cognitive impairment", Brain: A journal of neurology, 131(Pt 3), 2008, pp. 1-33 (Year: 2008).*

* cited by examiner

COMPUTER AIDED DIAGNOSIS SYSTEM FOR MILD COGNITIVE IMPAIRMENT

FIELD OF THE INVENTION

This application claims the benefit of U.S. provisional patent application Ser. No. 62/747,716, filed Oct. 19, 2018, for COMPUTER AIDED DIAGNOSIS SYSTEM FOR MILD COGNITIVE IMPAIRMENT, incorporated herein by reference.

FIELD OF THE INVENTION

A non-invasive computer-aided diagnosis system generates a diagnosis of mild cognitive impairment, a disease state which often leads to the development of Alzheimer's disease. The system uses as inputs both functional positron emission tomography and structural magnetic resonance imaging data, reconstructs a model of the patient's cortex, uses machine-learning techniques to generate probabilities for mild cognitive impairments for local cortical regions, uses machine-learning techniques to fuse the local diagnoses to generate a global diagnosis based on each imaging modality, then uses machine-learning techniques to fuse the modality-specific global diagnoses to generate a final global diagnosis.

BACKGROUND OF THE INVENTION

Alzheimer's disease (AD) is one of the most widely known neurodegenerative disorders that faces the central nervous system (CNS). The characteristics of AD are grouped into clinical and pathological features. These features vary from one patient to another. Clinically, AD patients show progressive deficits in cognition in addition to disturbances in thought, perception, and behaviors. Pathologically, patients incur neuronal loss, granulovacuolar degeneration, and the formation of the two main AD identifiers, neurofibrillary tangles and neuritic amyloid-beta (Aβ) plaques.

AD progresses through three stages: early (mild), intermediate (moderate), and late (severe). Discovering the disease in its early stage is the most challenging task due to the fact that pathological features appear 10-15 years prior to the earliest clinical symptoms. Additionally, the variability of the disease's features among patients represents an obstacle that hinders early diagnosis.

Mild cognitive impairment (MCI) is defined by more severe levels of cognitive impairments than that expected from normally aging people considering their education levels. This degree of impairment may affect one or more of the cognitive domains containing: memory, language, attention, executive function or visuospatial skills. Despite these impairments, the sufferer can still perform his or her daily activities (e.g., social or occupational functions) without any interference. Therefore, MCI is treated as an intermediate stage between normal aging based cognitive impairment and dementia-related severe impairment. Although not all MCI cases proceed to AD, it was found that MCI increases the risk of later developing AD.

Several different tests can be used for the diagnosis of AD, including mental/physical status, urine, blood, neurology, neuropsychology, and the patient's psychiatric and medical history. In addition, various types of brain imaging are also included in the diagnostic tests. Brain imaging plays a massive role in numerous research efforts due to its capabilities of identifying structural abnormalities, uncovering the metabolic abnormalities even with the absence of or uncharacteristic structural abnormalities, and showing both the locations and degrees of the detected atrophies.

Recently, structural magnetic resonance imaging (sMRI) has become one of the most developed modalities that provides substantial assistance in different pathological diagnoses due to its ability to show a detailed depiction of the body. sMRI has the ability to discriminate between the tissues through capturing proton density or magnetization properties (using spin-spin (T2) or spin-lattice (T1) relaxation times). This ability assists in revealing differences and changes between tissues with similar densities. The relaxation time constants are highly dependent on the tissue, which leads to excellent soft-tissue contrast. Additionally, sMRI has the ability to visualize soft tissues non-invasively. Regarding AD, sMRI is a non-invasive analysis tool that can examine the structural MCI-related decline throughout the progression of AD. sMRI analyses reveal the association between the atrophies that aid in predicting the future memory decline of a healthy adult and the increased development risks of AD.

In contrast to the structural assessment of the body with sMRI, emission-computed tomography (ECT) methodologies such as positron emission tomography (PET) address the body's physiology (i.e., function). In PET scans, a pair of photons is produced in each annihilation between a positron emitted from an injected radioactive tracer isotope and an electron in the body. PET imaging of Aβ has been a major clinical tool for AD diagnosis, although there is a potential for misdiagnosis due to Aβ elevation associated with normal aging. Despite this caveat, carbon-11-labeled Pittsburgh compound B ($^{11}C$ PiB) tracer has shown considerable assistance in AD studies. PiB radiotracer is a fluorescent analog of thioflavin T that helps in visualizing the pathological hallmarks related to AD and consequently helps in investigating the deterioration during AD progression. Besides the PiB radiotracer, fludeoxyglucose (FDG), another common tracer, is also utilized in AD research. FDG is a metabolic marker that helps the PET studies to assess the regional cerebral metabolism. FDG-PET measures the glucose metabolism across the brain, which can aid in the prediction of patients' conversion from MCI to AD, since severe reductions in glucose consumption in the brain is a hallmark of individuals suffering from AD as compared to age-matched, normal control (NC) individuals.

Previous brain imaging studies proposed a global diagnosis of AD, and most of these works utilized FDG-PET scans. Although automated global diagnosis systems can assist experts in their diagnosis and treatment procedures, a detailed, regional-based diagnosis system can provide more assistance. This is due to the variability of disease manifestation that hinders the early diagnosis of AD. Also, a detailed regional diagnosis provides more help in uncovering the spectrum of the disease.

SUMMARY

The present invention aims to address the personalized diagnosis of AD through presenting a detailed regional based computer-aided diagnosis (CAD) system for the early diagnosis of AD in the MCI stage. For this purpose, the diagnosis is based on two known AD-related biomarkers: functional PET imaging of Aβ plaques and structural sMRI. For each modality, diagnoses for local regions of the cortex (also referred to as local or regional diagnoses) are produced using a probabilistic support vector machine (pSVM) Then, a global diagnosis is produced using a standard SVM that takes a fusion of the results from each modality. This global diagnosis reflects a more comprehensive assessment of the early signs of AD based upon the combined functional and the structural analyses of the brain.

In some embodiments, the present invention comprises a computer aided diagnostic system for diagnosis of a disease state, including at least one non-transitory computer readable storage medium having computer program instructions stored thereon and at least one processor configured to execute the computer program instructions causing the processor to perform the following operations: constructing a map of the subject brain based at least in part on functional medical imaging data of a subject brain and structural medical imaging data of the subject brain; parcellating the map into a plurality of regions; extracting, for each region in the map, at least one functional feature from the functional medical imaging data; generating, for each region in the map, a first probability of disease state, wherein the first probability for each region in the map is based at least in part on the extracted functional feature from that region; generating a first global diagnosis by fusing the first probabilities of disease state in each region of the map; extracting, for each region in the map, at least one of a geometric feature and a shape feature from the structural medical imaging data; generating, for each region in the map, a second probability of disease state, wherein the second probability for each region in the map is based at least in part on the extracted geometric feature or shape feature from that region; generating a second global diagnosis by fusing the second probabilities of disease state in each region of the map; and generating a final global diagnosis of disease state or normal condition by fusing the first global diagnosis and the second global diagnosis. In some embodiments, the disease state is mild cognitive impairment or Alzheimer's disease. In further embodiments, the first probability of disease state and the second probability of disease state are generated, for each region in the map, using machine learning techniques. In certain embodiments, the first probability of disease state and the second probability of disease state are generated, for each region in the map, using a probability support vector machine. In some embodiments, the first global diagnosis and the second global diagnosis are generated using a support vector machine. In further embodiments, the final global diagnosis is generated using a support vector machine. In certain embodiments, the structural medical imaging data are sMRI scans of the subject brain. In some embodiments, the functional medical imaging data are PET scans of the subject brain. In further embodiments, the PET scans are $^{11}$C PiB PET scans. In certain embodiments, the geometric feature includes at least one of bounding box, perimeter, and volume, and wherein the shape feature includes at least one of Gaussian curvature, mean curvature, sharpness, and curvedness. In some embodiments, the functional feature is the incidence of amyloid-beta plaques.

In other embodiments, the present invention comprises a method for classifying a brain, the method including processing image data including a subject brain to generate a map of the subject brain parceled into a plurality of regions; parcellating the map into a plurality of regions; extracting, for each region, at least one functional feature; generating, for each region in the map, a first probability of a condition, wherein the first probability for each region in the map is based at least in part on the extracted functional feature from that region; generating a first global classifier by fusing the first probabilities of the condition in each region of the map; extracting, for each region in the map, at least one of a geometric feature and a shape feature; generating, for each region in the map, a second probability of the condition, wherein the second probability for each region in the map is based at least in part on the extracted geometric feature or shape feature from that region; generating a second global classifier by fusing the second probabilities of the condition in each region of the map; and classifying the subject brain based on the first global classifier and the second global classifier. In some embodiments, classifying the subject brain includes classifying the subject brain as being indicative of Alzheimer's disease based on fusing the first global classifier and the second global classifier. In further embodiments, classifying the subject brain includes classifying the subject brain as being indicative of mild cognitive impairment based on fusing the first global classifier and the second global classifier. In certain embodiments, the map is based at least in part on functional medical imaging data of the subject brain and structural medical imaging data of the subject brain. In some embodiments, the structural medical imaging data are sMRI scans of the subject brain. In further embodiments, the functional medical imaging data are $^{11}$C PiB PET scans of the subject brain. In certain embodiments, the geometric feature includes at least one of bounding box, perimeter, and volume, and wherein the shape feature includes at least one of Gaussian curvature, mean curvature, sharpness, and curvedness. In some embodiments, the functional feature is the incidence of amyloid-beta plaques.

It will be appreciated that the various systems and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

DETAILED DESCRIPTION OF THE PREFERRED EMBODIMENTS

Figure 1:
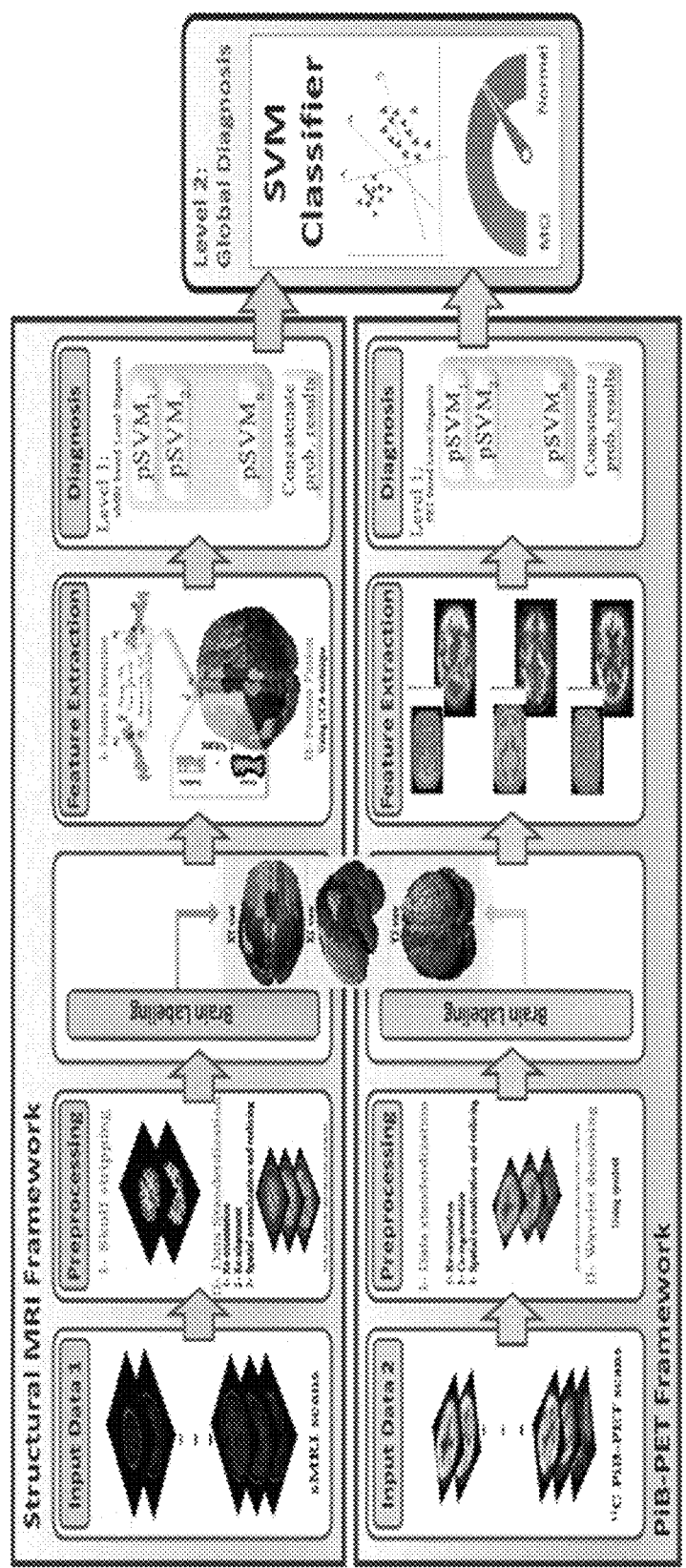
FIG. 1 is a schematic diagram depicting the sMRI-based CAD subsystem for the early diagnosis of AD.

The present invention aims to address the personalized diagnosis of AD through presenting a regional-based CAD system for the early diagnosis of AD in the MCI stage. For this purpose, the diagnosis is based on two well-known AD-related biomarkers, which are PET imaging of Aβ and sMRI. Data from these two modalities are fused to provide complementary information to aid in a personalized diagnosis based on functional and structural assessments. As shown in FIG. 1, the $^{11}$C PiB-PET scans are analyzed to produce two functional based diagnosis levels (regional diagnoses followed by modality-based global diagnosis). Second, the sMRI scans are also analyzed to produce two structural based diagnosis levels (regional diagnoses followed by modality-based global diagnosis). Third, the modality-based global results are fused using machine-learning techniques to generate a final global diagnosis of MCI or NC.

Starting with PET Aβ imaging, $^{11}$C PiB-PET scans were used to demonstrate the first analysis sub-system that has five stages. First, the scans are preprocessed to standardize them to the labeling atlas space, in some embodiments, Montreal Neurological Institute (MNI) space, and enhance their quality using a wavelet-based de-noising process. Second, the parcellation process is performed using an automatic anatomical labeling (AAL) atlas to partition the brain into 116 different regions to serve the regional diagnosis purpose. Third, relying on the fact that significantly greater retention of PiB in a brain region is linked with greater incidence of amyloid-beta (Aβ) plaques within that region, Laplacian of Gaussian (LoG) with automatic scale selection is applied to reveal AD-related abnormalities in each region separately. Fourth, a regional diagnosis of the likelihood of amyloid-beta plaques is produced for each brain region using a pSVM, followed by a global diagnosis wherein a standard SVM is used to integrate the regional diagnoses and classify the subject as NC or MCI based on the PET medical imaging data.

The second sub-system of the CAD system, which utilizes sMRI scans, also has five steps. First, the scans are preprocessed, to standardize them to the labeling space as well as stripping the skull from them. Second, the parcellation process takes place through applying the AAL atlas. Third, a plurality of geometric- and shape-based properties of the images are extracted and fused through applying canonical correlation analysis (CCA) based technique, to produce more informative/representative features to be used in the diagnosis step. Fourth, the significant brain regions whose features significantly differ in MCI with respect to NC is determined through two-sample t-test with Bonferroni correction for multiple comparisons. Fifth, both the pSVM as well as the standard SVM are again employed to produce significant regions-based diagnosis followed by the structural sMRI modality-based global diagnosis.

Finally, the two modality-based global diagnoses generated by the two subsystems are fused using SVM to generate a final global diagnosis of MCI or NC based on the structure and function of the brain.

Providing additional detail to the above summary, anatomical brain labeling is applied to the scans to assess local/regional diagnosis. Therefore, the scans are standardized first to the labeling atlas template's space, the Montreal Neurological Institute (MNI) space, through a number of steps: data re-orientation, co-registration, spatial normalization, and re-slicing (Algorithm 1).

Algorithm 1: Standardization steps of both $^{11}$C PiB-PET and sMRI scans Input: Original $^{11}$C PiB-PET and sMRI scans with their corresponding masks Output: Standardized/atlas-matched scans Procedures: 1. Strip the skull of the sMRI scans through convolution with their masks obtained from ADNI database.

2. Re-orient both modalities to the AC-PC line, an imaginary line between the anterior and posterior commissures, as follows:
  (a) Pick and re-orient one of the sMRI scans (the reference scan) to the AC-PC line.
  (b) Use the resulting re-oriented scan to re-orient the equivalent $^{11}$C PiB-PET scan taken at the same angle and depth (and consequently the remaining sMRI scans).
  (c) Apply the resulting re-orientation matrix of the PET scan to the remaining $^{11}$C PiB-PET scans.
  (d) Apply the rigid body transformation (i.e., translation, rotation, and mutual information cost function) to co-register both the sMRI and the $^{11}$C PiB-PET modalities.
3. Spatially normalize as well as re-slice the scans to match the space of the atlas template (MNI space).
4. Denoise the $^{11}$C PiB-PET.

Starting with the sMRI scans, before performing the standardization steps, the scans need to undergo skull stripping operation. To achieve this task, the scans were convolved with their binary brain masks obtained from the Alzheimer's Disease Neuroimaging Initiative (ADNI). After performing this step, the sMRI scans, as well as the $^{11}$C PiB-PET scans, were ready to be standardized. Starting with re-orienting the scans (i.e., sMRI and $^{11}$C PiB-PET based scans), this operation was done with respect to the AC-PC line and matched the orientation of the scan to that of the atlas template. Then, using a least squares approach, the six-degrees-of-freedom was estimated, and rigid body spatial transformation applied to match the brain as closely as possible with the atlas. First, an sMRI scan (reference) was selected and re-oriented to the AC-PC line, and then the target scans were re-oriented and re-aligned (i.e., the corresponding $^{11}$C PiB-PET scan, and consequently the remaining $^{11}$C PiB-PET scans, in addition to all the remaining sMRI scans) to the reference scan. The second step was achieved by utilizing the matrix of the re-orientation and the rigid-body transformations in the form of translations, as well as rotations along with the mutual information based cost function and $7^{th}$ degree B-spline interpolation method. Any of the sMRI scans can be used as a reference scan as all the scans in ADNI have broadly the same spatial orientation. One of the sMRI scans was chosen as a reference due to the high resolution of the sMRI as compared with the $^{11}$C PiB-PET scans.

Spatial normalization using the algorithm of Ashburner, J. and Friston, K. J., Unified segmentation. NeuroImage 26, 839-851 (2005) and re-slicing using rigid-body transformations were applied to the resulting re-oriented/re-aligned scans using full affine transformation to translate, shear, rotate, and zoom the scans. In addition, nonlinear deformations were performed in order to achieve precise alignment with the MNI standard, thereby producing a 3D map of the subject brain based on the structural sMRI imaging data and functional $^{11}$C PiB-PET imaging data. After data standardization, the $^{11}$C PiB-PET scans went through a de-noising operation to retain the details of the image while removing artifacts that could result during the image acquisition process or/and transmission. For this purpose, the wavelet denoising was used due to its good localization characteristic. Also, symlet8 mother wavelet was used due to its role as a compact support wavelet of least asymmetry and the highest number of the support width's vanishing moments. This approach helps to locally preserve the spatial aspects of the image.

After preprocessing and standardizing the scans, the next step is to extract the cortex through using a parcellation of the scans with a regional, detailed labeling atlas of the brain, such AAL atlas, a hemisphere-based labeling atlas. The AAL atlas parcellates the brain into 116 anatomical regions defined in part by the pattern of sulci in the MNI standard single subject's brain, including 90 cerebral regions in both hemispheres and 26 cerebellar regions. In some embodiments, this step is performed for both modalities using the xjview toolbox of MATLAB to define the AAL-based anatomical regions.

After extracting the cortex, the next step is to extract the discriminant features to be used for diagnostic purposes. Different feature extractors are used for each modality. For sMRI, where the aim is to reveal characteristics of brain structure indicative of AD, several geometric (i.e., bounding box, perimeter, and volume) and shape (Gaussian curvature, mean curvature, sharpness, and curvedness) features were calculated. The bounding box aims to determine the smallest rectangle that encloses the brain region producing a vector that contains the coordinates of the upper-left corner and the width of the obtained bounding box. The perimeter aims to determine the distance around the region's boundary by finding the distance between the adjacent pair of pixels that surrounds the region's border. The bounding box and perimeter were calculated for each slice of each region then the mean was calculated for the entire region's 3D volume. After extracting these features, to obtain the volume as well as the shape features, a reconstruction process of each region is performed first. The marching cubes (MC) algorithm was applied for isosurface extraction due to its ability to produce high-resolution results. Algorithm 2 presents the steps of extracting the shape features. Beside these shape features, the volume was calculated for each reconstructed region as well. Atrophy of brain regions is a biomarker for AD and MCI, and quantification of these geometric and shape features allows for automated evaluation of the presence or absence of atrophy using a plurality of indicators. However, despite considering the volume as the most well-known, cross-sectional quantitative metric of AD, the variability related to the individuals' demography can end up biasing its results. Therefore, the volume was utilized in combination with other features to avoid bias and to obtain more precise results.

Algorithm 2: Extraction of shape-based features from sMRI scans

Input: Each labeled sMRI-based anatomical brain region

Output: Shape-based features (curvatures, sharpness, and curvedness)

Procedures: 1. Use the volume lattice to define cubes ($C_I$) where the cubes vertices of the corner $V_I$ are defined through the points ($P(x_i, y_j, s_k)$) of the lattice for column $x_i(\forall_i)$, $y_i(\forall_i)$ and slice $S_k(\forall_n)$:n is the number of slices.

2. In a cube-by-cube manner (i.e., a sequential processing) and throughout the rows of the dataset, build a fecetized isosurface. During this, mark each $V_i$ when it has a greater than or equal value compared to the isovalue a and keep the remaining vertices unmarked.

3. Define the "active" edge $E_j$ of the cube as the edge that the isosurface intersects with, where $E_j$ is terminated by a marked vertex $V_jm$ and an unmarked vertex $V_ju$.

4. A factorization process is then applied to the interacted isosurface through a look-up table that contains the intersection topologies where the linear interpolation is applied for estimating the isosurface-edge intersection location I=($I_x, I_y, I_s$) as:

$$I(x,y,s) = V_{m(x,y,s)} + \rho(V_{u(x,y,s)} - V_{m(x,y,s)})$$

where $$\rho = \frac{\alpha - L_m}{L_u - L_m},$$

where: $L_m$ and $L_u$ are the scalars values $V_m$ as well as $V_u$, respectively.

5. Utilize the extracted isosurface, triangulated mesh, to calculate the curvature based features through the following equations:

$$C_{Gaussian} = \lambda_1 \lambda_2 \quad (1)$$

$$C_{mean} = \tfrac{1}{2}(\lambda_1 + \lambda_2) \quad (2)$$

$$\text{Sharpness} = (\lambda_1 - \lambda_2)^2 \quad (3)$$

$$\text{Curvedness} = \sqrt{((\lambda_1^2 + \lambda_2^2)/2)} \quad (4)$$

where $\lambda_1$ and $\lambda_2$ are the principal curvatures, or eigenvalues of the shape operator, estimated at each node of the mesh.

To maximize the representative information, a feature fusion procedure, relying on the CCA technique, was applied to extracted features. CCA was chosen due to its role in addressing the relationship between two variable sets through finding the linear combinations that maximize the pair-wise correlations between the sets. Here, the CCA was utilized sequentially by fusing two features at a time until ending up with the final vector of the fused features. Put another way, the three geometric features and four shape features were fused into a single final vector and that final vector was used to determine the regional classification of MCI or NC.

For feature extraction for $^{11}$C PiB-PET scans, each of the labeled regions was analyzed using the scale-invariant blob detection method employing LoG filters with automatic scale selection. Blob detection is used to highlight circular structures (i.e., blobs) from the images and present them as a feature, where the blob, in general, is a local minimum or maximum intensity with a radially symmetric distribution. Here, the local maxima intensity-based blobs are extracted and used to detect AD related abnormalities since AD has high significant retention of PiB in the brain regions that have increased Aβ plaques.

After separately determining the significant regions of the sMRI and PiB-PET scans, the features of the cortical regions are then used to construct the classifiers that in turn will produce regional and global diagnoses. In the first level, for each region in each imaging modality, a separate probabilistic SVM (pSVM) is utilized to produce a probabilistic result that reflects the severity of the disease (i.e., NC or MCI) in the region. These regional results are concatenated to determine a global probabilistic result for each modality, i.e, a first global diagnosis based on PET functional medical imaging data and a second global diagnosis based on sMRI structural medical imaging data). Then, in the second level, the maximum of the obtained probabilistic results for both modalities is input to a standard SVM to generate the final global diagnosis of NC or MCI for the subject.

The disclosed CAD system provides local/regional diagnoses of AD based on structural medical imaging scan and functional medical imaging scans, combines these regional diagnoses into two global diagnoses, one based on each imaging modality, then combines these into a final global diagnosis based on both imaging modalities. The dataset used for validation of the present invention contains $^{11}$C PiB-PET and sMRI scans of a total of 84 subjects with 19

NC, and 65 MCI where Table 1 shows the demographic data of these subjects. The dataset was obtained from ADNI database. To determine the memory functions based normality/abnormality of the participants with respect to their education level, a subset of the Wechsler Memory Scale (WMS), called the Logical Memory II, was used. Regarding the used groups, NC group consists of the subjects with no depression, cognitive impairment, or dementia signs while the MCI group includes the subjects who have been reported through themselves, an informant or a clinician to have subjective memory concerns. The subjects of the last group did not show either significant levels of cognitive impairment or any other signs related to dementia. All the available baseline scans of the MCI group were included regardless of whether these subjects ultimately converted to AD.

TABLE 1

The demographical data of the used sMRI and PET scans.

| (N = 84) | Average Age ± SD | Gender N (%) Male | Female | WMS Logical Memory II results (based on years of education) ≥16 years | 8-15 years | 0-7 years |
|---|---|---|---|---|---|---|
| NC (19) | 78.3 ± 5.01 | 11 (57.89) | 8 (42.1) | ≥9 | ≥5 | ≥3 |
| MCI (65) | 75.78 ± 7.67 | 44 (67.69) | 21 (32.30) | ≥8 | ≥4 | ≥2 |

Figure 2:
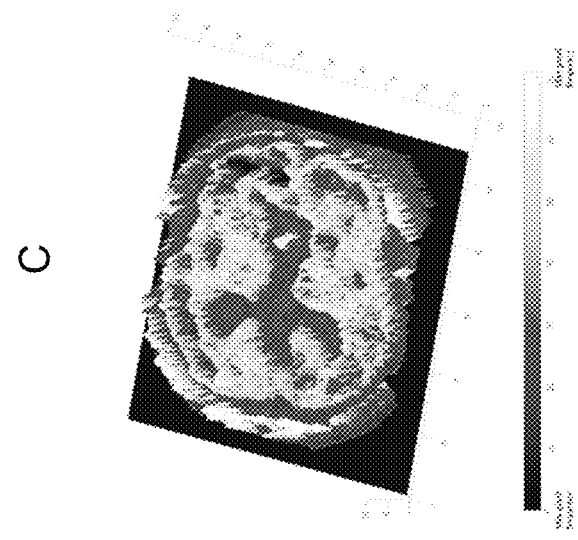
FIG. 2 depicts (A) a PiB-PET scan (B) blob features, identified by plus signs, extracted from the scan using the Laplacian of Gaussian (LoG) method, and (C) a slice view of a 3D histogram of the scan.
Figure 2:
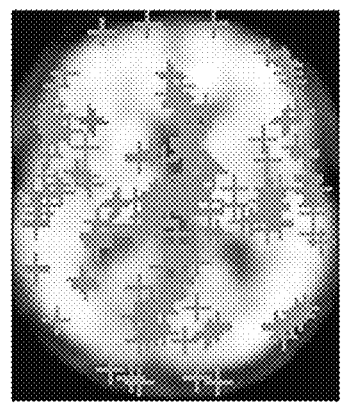
Figure 2:
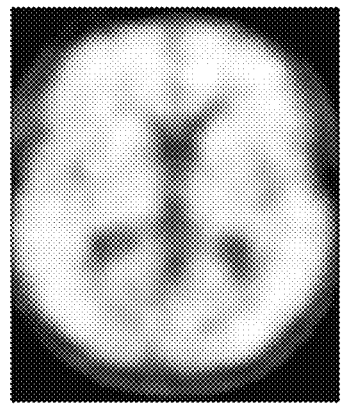
Figure 3:
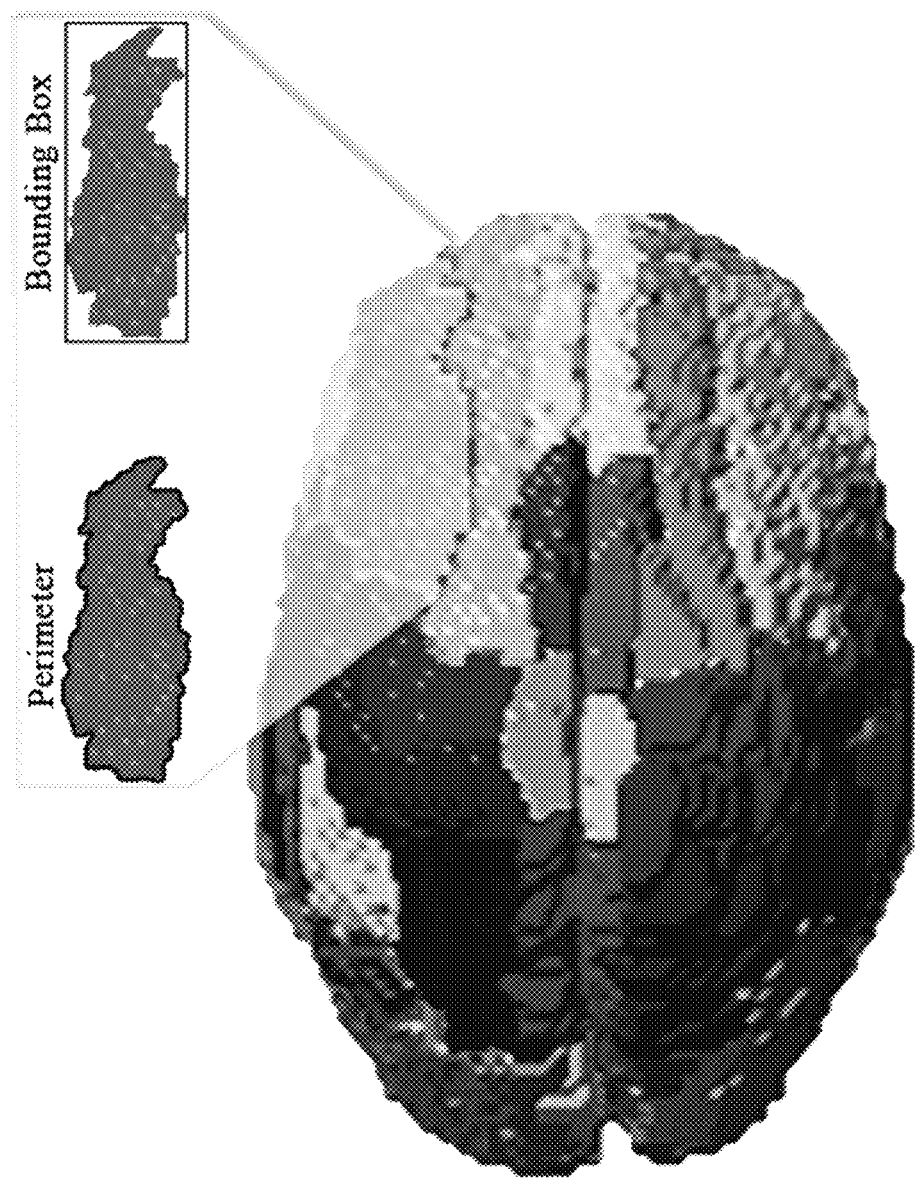
FIG. 3 depicts a sMRI scan with identified perimeter and bounding box features.
Figure 4A:
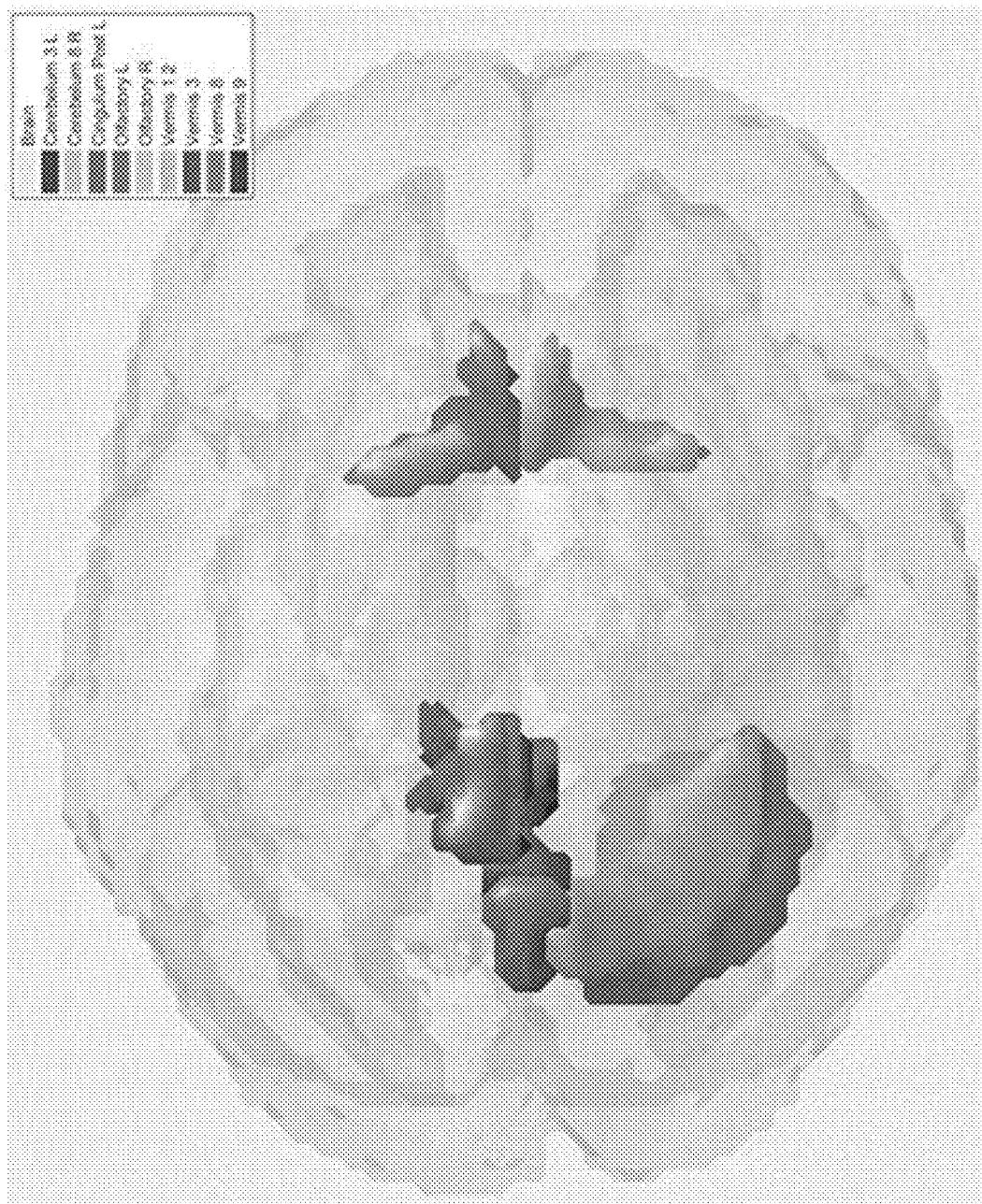
FIG. 4A depicts the statistically significant regions for discriminating MCI vs. NC in a PiB-PET brain scan.
Figure 4B:
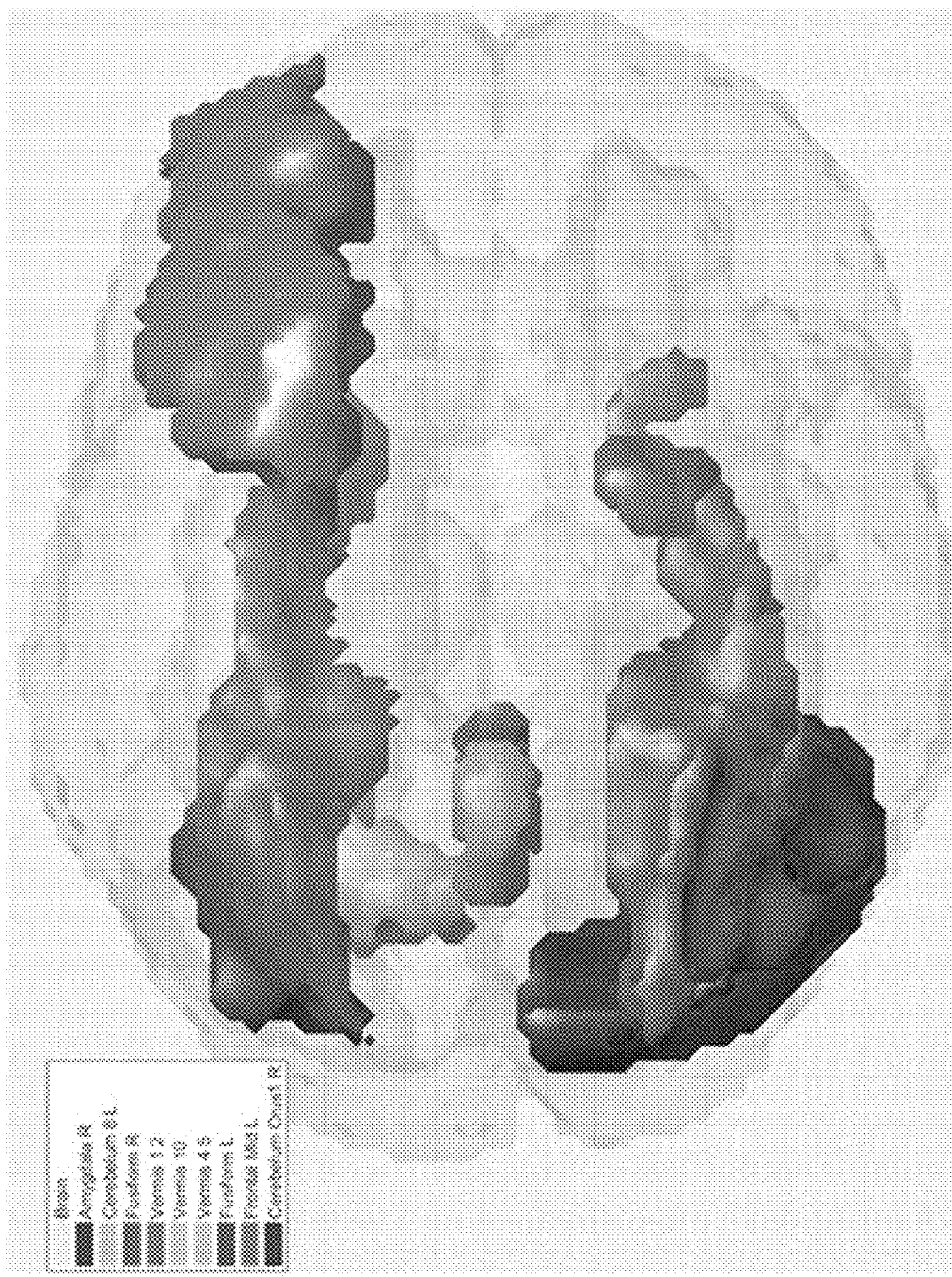
FIG. 4B depicts the statistically significant regions for discriminating MCI vs. NC in a sMRI brain scan.

Starting with the feature extraction, FIG. 2 shows an example of the PiB-PET scans-based features while FIG. 3 illustrates the idea behind each of the sMRI based features. FIG. 2 illustrates the detected blobs where the 3D histogram visualizes the role of the blob detector in the feature extraction process. After obtaining the regions-based features, the statistical analysis process takes place to provide a significant/precise diagnosis in addition to enhancing the performance results as shown in Table 2. Regarding the PiB-PET scans, the obtained significant regions are: Cerebelum_3_L, Cerebelum_8_R, Cingulum_Post_L, Olfactory_L, Olfactory_R, Vermis_1_2, Vermis_3, Vermis_8, and Vermis_9. For sMRI, the significant regions that have found are: Amygdala_R, Cerebelum_8_L, Fusiform_R, Vermis_1_2, Vermis_10, Vermis_4_5, Fusiform_L, Frontal_Mid_L, and Cerebelum_Crus1_R. FIG. 4 visualizes the aforementioned significant regions that have been identified in both modalities.

Two different tests were performed to evaluate the diagnosis performance of the CAD system. The first test assessed the performance of each modality-based global diagnosis with the final global diagnosis. This evaluation was performed using leave-one-subject-out (LOSO) and K-fold validation methods, and the results shown in Table 2. Linear kernel was used to construct the utilized pSVM/SVM classifiers due to its superior results as compared with the other kernels (i.e., polynomial and radial basis function (RBF) kernels).

TABLE 2

System evaluation when using each of the modalities alone and when integrating their global diagnosis using leave-one-subject-out and K-fold cross validation methods.

| | $^{11}$C PiB-PET scans | | | sMRI | | | Fusion of both modalities | | |
|---|---|---|---|---|---|---|---|---|---|
| | | K-fold | | | K-fold | | | K-fold | |
| | LOSO | K = 2 | K = 4 | LOSO | K = 2 | K = 4 | LOSO | K = 2 | K = 4 |
| ACC | 100 | 97.61 | 98.8 | 78.57 | 73.81 | 76.2 | 100 | 97.61 | 98.8 |
| Spec. | 100 | 94.73 | 94.73 | 47.36 | 47.36 | 52.63 | 100 | 94.73 | 94.73 |
| Sens. | 100 | 98.46 | 100 | 87.7 | 81.63 | 83.1 | 100 | 98.46 | 100 |

The second test compared the accuracy, specificity, and sensitivity of the SVM-based system disclosed herein to that of state-of-the-art classifiers, namely, naïve Bayes (NB), Random Forest (RF), Deep Learning (DL), and Decision Tree (DT), as shown in Table 3. The linear kernel was used to construct the proposed system due to its general superior performance as compared with other SVM kernels. The architecture of the DL comparison classifier was a multi-layer feed-forward artificial neural network (ANN), which was trained with stochastic gradient descent using back-propagation. It is important to note that when constructing the applied classifiers, their parameters were optimized to produce their final performance results as follow: (i) for the DT, the maximum depth of a tree was 2; (ii) for the RF the optimal number of trees was found to be 60 while their maximum depth was 4; (iii) for the SVM, the kernel gamma was 0.01 and the optimal complexity constant, the misclassification tolerance, was 10. Table 3. Comparison between the disclosed SVM-based system with other state-of-the-art classifiers using LOSO and K-fold validation.

TABLE 3

Comparison between the disclosed SVM-based system with other state-of-the-art classifiers using LOSO and K-fold validation.

|  |  | LOSO | K = 2 | K = 4 | K = 10 |
|---|---|---|---|---|---|
| NB | ACC | 93.83 | 98.78 | 100 | 98.75 |
|  | Spec. | 84.21 | 94.74 | 100 | 94.74 |
|  | Sens. | 96.77 | 100 | 100 | 100 |
| DL | ACC | 93.83 | 85.21 | 92.5 | 91.39 |
|  | Spec. | 73.68 | 57.89 | 73.68 | 73.68 |
|  | Sens. | 100 | 93.55 | 98.39 | 96.77 |
| DT | ACC | 92.59 | 100 | 100 | 100 |
|  | Spec. | 68.42 | 100 | 100 | 100 |
|  | Sens | 100 | 100 | 100 | 100 |
| RF | ACC | 100 | 96.31 | 98.75 | 98.75 |
|  | Spec. | 100 | 89.47 | 94.74 | 94.74 |
|  | Sens. | 100 | 98.39 | 100 | 100 |
| Proposed system | ACC | 100 | 97.5 | 100 | 100 |
|  | Spec. | 100 | 100 | 100 | 100 |
|  | Sens. | 100 | 96.77 | 100 | 100 |

Figure 5:
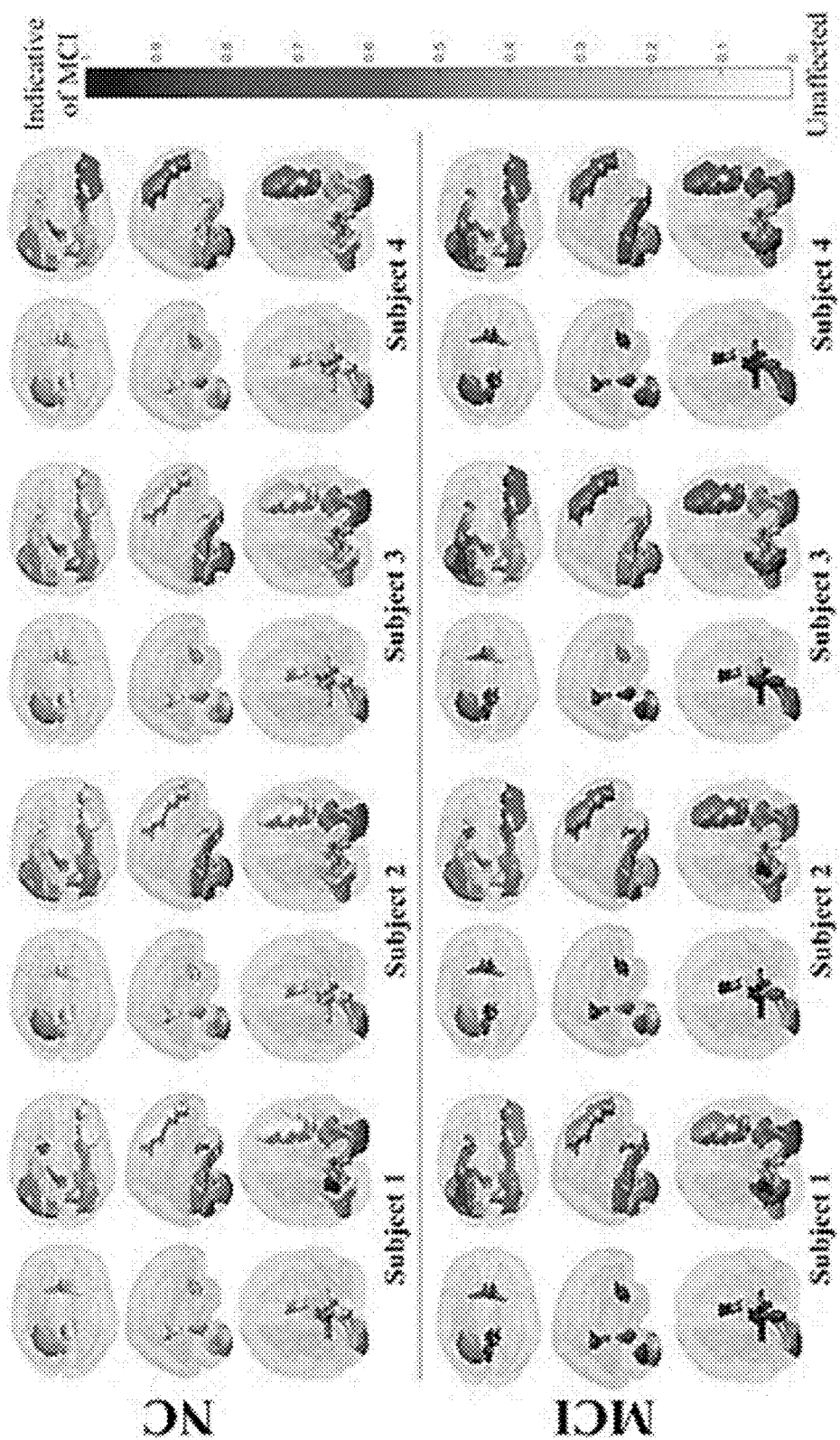
FIG. 5 depicts regional diagnoses of (a) NC and (b) MCI, where the shade gradient indicates probability of MCI in each region. Six brain scans are displayed for each subject, the left column of brain scans displaying the results from the functional (PET) assessment and the right column of brain scans displaying the results from the structural (sMRI) assessment.

FIG. 5 shows examples of the regional diagnosis results for different subjects, four MCI and four NC. Six brain scans are displayed for each subject, the left column of brain scans displaying the results from the functional (PET) assessment and the right column of brain scans displaying the results from the structural (sMRI) assessment. The shade gradient indicates probability of MCI in each region. Relying on this visualization, the specialist can have complementary information from two sources; PET scans that shows the functional-based influence of the disease and the sMRI that shows its impact on the structure of the brain. Relying on this visualization, the specialist can determine the probability of local abnormality which can consequently assist in determining the direction of treatment.

The disclosed CAD system may be embodied in computer program instructions stored on a non-transitory computer readable storage medium configured to be executed by a computing system. The computing system utilized in conjunction with the computer aided diagnostic system described herein will typically include a processor in communication with a memory, and a network interface. Power, ground, clock, and other signals and circuitry are not discussed, but will be generally understood and easily implemented by those ordinarily skilled in the art. The processor, in some embodiments, is at least one microcontroller or general purpose microprocessor that reads its program from memory. The memory, in some embodiments, includes one or more types such as solid-state memory, magnetic memory, optical memory, or other computer-readable, non-transient storage media. In certain embodiments, the memory includes instructions that, when executed by the processor, cause the computing system to perform a certain action. Computing system also preferably includes a network interface connecting the computing system to a data network for electronic communication of data between the computing system and other devices attached to the network. In certain embodiments, the processor includes one or more processors and the memory includes one or more memories. In some embodiments, computing system is defined by one or more physical computing devices as described above. In other embodiments, the computing system may be defined by a virtual system hosted on one or more physical computing devices as described above.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A computer aided diagnostic system for diagnosis of a disease state, the system comprising,
    at least one non-transitory computer readable storage medium having computer program instructions stored thereon; and
    at least one processor configured to execute the computer program instructions causing the processor to perform the following operations:
    constructing a map of the subject brain based at least in part on functional medical imaging data of a subject brain and structural medical imaging data of the subject brain;
    parcellating the map into a plurality of regions;
    extracting, for each region in the map, at least one functional feature from the functional medical imaging data;
    generating, for each region in the map, a first probability of disease state, wherein the first probability for each region in the map is based at least in part on the extracted functional feature from that region;
    generating a first global diagnosis by fusing the first probabilities of disease state in each region of the map;
    extracting, for each region in the map, at least one of a geometric feature and a shape feature from the structural medical imaging data;
    generating, for each region in the map, a second probability of disease state, wherein the second probability for each region in the map is based at least in part on the extracted geometric feature or shape feature from that region;
    generating a second global diagnosis by fusing the second probabilities of disease state in each region of the map; and
    generating a final global diagnosis of disease state or normal condition by fusing the first global diagnosis and the second global diagnosis.

2. The system of claim 1, wherein the disease state is mild cognitive impairment.

3. The system of claim 1, wherein the disease state is Alzheimer's disease.

4. The system of claim 1, wherein the first probability of disease state and the second probability of disease state are generated, for each region in the map, using machine learning techniques.

5. The system of claim 1, wherein the first probability of disease state and the second probability of disease state are generated, for each region in the map, using a probability support vector machine.

6. The system of claim 1, wherein the first global diagnosis and the second global diagnosis are generated using a support vector machine.

7. The system of claim 1, wherein the final global diagnosis is generated using a support vector machine.

8. The system of claim 1, wherein the structural medical imaging data are sMRI scans of the subject brain.

9. The system of claim 1, wherein the functional medical imaging data are PET scans of the subject brain.

10. The system of claim 9, wherein the PET scans are $^{11}$C PiB PET scans.

11. The system of claim 1, wherein the geometric feature includes at least one of bounding box, perimeter, and volume, and wherein the shape feature includes at least one of Gaussian curvature, mean curvature, sharpness, and curvedness.

12. The system of claim 1, wherein the functional feature is the incidence of amyloid-beta plaques.

13. A method for classifying a brain, the method comprising
processing image data including a subject brain to generate a map of the subject brain parceled into a plurality of regions;
parcellating the map into a plurality of regions;
extracting, for each region, at least one functional feature;
generating, for each region in the map, a first probability of a condition, wherein the first probability for each region in the map is based at least in part on the extracted functional feature from that region;
generating a first global classifier by fusing the first probabilities of the condition in each region of the map;
extracting, for each region in the map, at least one of a geometric feature and a shape feature;
generating, for each region in the map, a second probability of the condition, wherein the second probability for each region in the map is based at least in part on the extracted geometric feature or shape feature from that region;
generating a second global classifier by fusing the second probabilities of the condition in each region of the map; and
classifying the subject brain based on the first global classifier and the second global classifier.

14. The method of claim 13, wherein classifying the subject brain includes classifying the subject brain as being indicative of Alzheimer's disease based on fusing the first global classifier and the second global classifier.

15. The system of claim 13, wherein classifying the subject brain includes classifying the subject brain as being indicative of mild cognitive impairment based on fusing the first global classifier and the second global classifier.

16. The system of claim 13, wherein the map is based at least in part on functional medical imaging data of the subject brain and structural medical imaging data of the subject brain.

17. The system of claim 16, wherein the structural medical imaging data are sMRI scans of the subject brain.

18. The system of claim 16, wherein the functional medical imaging data are $^{11}$C PiB PET scans of the subject brain.

19. The system of claim 13, wherein the geometric feature includes at least one of bounding box, perimeter, and volume, and wherein the shape feature includes at least one of Gaussian curvature, mean curvature, sharpness, and curvedness.

20. The system of claim 13, wherein the functional feature is the incidence of amyloid-beta plaques.

* * * * *